United States Patent
MacFarland et al.

(10) Patent No.: US 6,365,583 B1
(45) Date of Patent: Apr. 2, 2002

(54) METHODS TO ENHANCE WHITE BLOOD CELL COUNT

(75) Inventors: Ronald Trevor MacFarland, Vancouver (CA); Andrew W. Millar, Wallingford (GB); Gary Bridger, Bellingham, WA (US); Michael J. Abrams, Custer, WA (US); Geoffrey W. Henson, Ferndale, WA (US)

(73) Assignee: AnorMED, Inc., Langley, British Columbia ( * ) Notice: Subject to any disclaimer, the term of this patent is extended or adjusted under 35 U.S.C. 154(b) by 0 days.

(21) Appl. No.: 09/495,298

(22) Filed: Feb. 1, 2000

Related U.S. Application Data

(60) Provisional application No. 60/118,255, filed on Feb. 2, 1999.

(51) Int. Cl.[7] .................. A61K 31/33; C07D 245/00; C07D 255/02
(52) U.S. Cl. .................. 514/183; 540/473; 540/474
(58) Field of Search .................. 514/183; 540/474, 540/473

(56) References Cited

U.S. PATENT DOCUMENTS

| | | | |
|---|---|---|---|
| 5,021,409 A | 6/1991 | Murrer et al. | 514/183 |
| 5,582,823 A | 12/1996 | Souza | 424/85.2 |

(List continued on next page.)

FOREIGN PATENT DOCUMENTS

| | | |
|---|---|---|
| EP | 0 434 385 A | 6/1991 |

(List continued on next page.)

OTHER PUBLICATIONS

Veronese et al. Human retroviruses, 1992, Clinical virology Manual, 2nd Edition, Elsevier, pp. 585–597.*

(List continued on next page.)

Primary Examiner—Russell Travers
Assistant Examiner—S. Wang
(74) Attorney, Agent, or Firm—Morrison & Foerster LLP

(57) ABSTRACT

Methods to elevate white blood cell counts in animal subjects using compounds of formula (1) are disclosed. These compounds have the formula $$Z\text{-linker-}Z' \qquad (1)$$

or pharmaceutically acceptable salt thereof wherein Z is a cyclic polyamine containing 9–32 ring members of which 3–8 are nitrogen atoms, said nitrogen atoms separated from each other by at least 2 carbon atoms, and wherein said heterocycle may optionally contain additional heteroatoms besides nitrogen and/or may be fused to an additional ring system;

Z' may be embodied in a form as defined by Z above, or alternatively may be of the formula $$-N(R)-(CR_2)_n-X$$

wherein each R is independently H or straight, branched or cyclic alkyl (1–6C), n is 1 or 2, and X is an aromatic ring, including heteroaromatic rings, or is a mercaptan;

"linker" represents a bond, alkylene (1–6C) or may comprise aryl, fused aryl, oxygen atoms contained in an alkylene chain, or may contain keto groups or nitrogen or sulfur atoms;

in an amount effective to elevate said WBC count in said subject.

14 Claims, 2 Drawing Sheets

U.S. PATENT DOCUMENTS

| | | |
|---|---|---|
| 5,583,131 A | 12/1996 | Bridger et al. ............... 514/183 |
| 5,606,053 A | 2/1997 | Prashad et al. ............. 540/474 |
| 5,612,478 A | 3/1997 | Xu et al. ..................... 540/474 |
| 5,698,546 A | 12/1997 | Bridger et al. ............. 514/183 |
| 5,756,728 A | 5/1998 | Xu et al. ..................... 540/474 |
| 5,801,281 A | 9/1998 | Xu et al. ....................... 564/82 |
| 5,817,807 A | 10/1998 | Bridger et al. ............. 540/474 |

FOREIGN PATENT DOCUMENTS

| | | |
|---|---|---|
| WO | WO 95 18808 | 7/1995 |
| WO | WO 0002870 | 1/2000 |

OTHER PUBLICATIONS

Bridger, G. et al. (1995). "Synthesis and stucture—Activity Relationships of Phenylenebis(methylene)–Linked Bis–Tetraazamacrocyles that Inhibit HIY Replication. Effcets of Macrocyclic Ring Size and Substituents on the Aromatic Linker," *J Med Chem* 38:366–378.

Hunt, D. et al. (1993). "Photofrin, but not Benzoporphyrin Derivative, Stimulates Hermatopiesis in the Mouse," *Immunopharmacology* 26:203–212.

* cited by examiner

METHODS TO ENHANCE WHITE BLOOD CELL COUNT

This application claims priority to U.S. provisional patent application Ser. No. 60/118,255, filed on Feb. 2, 1999.

TECHNICAL FIELD

The invention is in the field of therapeutics and medicinal chemistry. More particularly, the invention concerns methods to enhance white blood cell counts in subjects by administering certain cyclic polyamines.

BACKGROUND ART

White blood cells play a significant part in maintaining the health and viability of animals, including humans. These white blood cells include neutrophils, macrophage, and basophils/mast cells as well the B and T cells of the immune system. White blood cells are continuously replaced (as are red blood cells and clot forming cells) by the hematopoietic system in response to a number of growth factors, such as colony stimulating factors (CSF) and various cytokines. The nucleotide sequences encoding a number of these growth factors have been cloned and sequenced. Perhaps the most widely known of these is granulocyte colony stimulating factor (G-CSF) which has been approved for use in counteracting the negative effects of chemotherapy. A discussion of the hematopoietic effects of this factor can be found, for example, in U.S. Pat. No. 5,582,823, incorporated in its entirety by reference herein.

While endogenous growth factors are pharmacologically effective, the well known disadvantages of employing proteins and peptides, as opposed to small molecules, as pharmaceuticals underlies the need to add to the repertoire of such growth factors compounds which are themselves small molecules. In another aspect, such small molecules are advantageous over proteins and peptides where production in large quantities are desired.

A number of cyclic polyamine antiviral agents have been described in a series of U.S. patents and applications over the last several years. These patents, U.S. Pat. Nos. 5,021,409; 5,583,131; 5,698,546; and 5,817,807 are incorporated herein by reference. Also incorporated by reference is copending application Ser. No. 09/111,895 filed Jul. 8, 1998, which describes additional compounds. These patents describe the structural characteristics of the cyclic polyamine antiviral agents.

In addition, improved methods for preparation of some of these compounds are described in U.S. Pat. Nos. 5,612,478; 5,756,728; 5,801,281; and 5,606,053. The disclosures of these U.S. patents are also incorporated herein by reference in their entirety.

It has now been found that the cyclic polyamine antiviral agents described in the above-mentioned patents have the effect of enhancing production of white blood cells as well as exhibiting antiviral properties. Thus, these agents are useful where treatment affects the activities within the bone marrow resulting in leukopenia, thus controlling the side-effects of chemotherapy, radiotherapy, enhancing the success of bone marrow transplantation, enhancing wound healing and burn treatment, as well as combating bacterial infections in leukemia.

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are incorporated in their entirety by reference herein.

DISCLOSURE OF THE INVENTION

The invention is directed to methods of treating animal subjects, in particular, veterinary and human patients, who are defective in white blood cell (WBC) count, or who would benefit from elevation of WBC levels. The methods of the invention employ cyclic polyamines including those described in the patents incorporated hereinabove by reference.

In one aspect, therefore, the invention is directed to a method to elevate the white blood cells (WBC) count, in a subject in need of such WBC elevation, which method comprises administering to said subject an amount of a compound of formula (1) or of a pharmaceutical composition thereof effective to elevate WBC levels.

In additional aspects, the invention is directed to pharmaceutical compositions containing the compound of formula (1) for use in effecting WBC count elevation in animal subject.

The compounds of formula (1) are of the formula:

Z-linker-Z'     (1)

wherein Z is a cyclic polyamine containing 9–32 ring members of which 3–8 are nitrogen atoms;

said nitrogen atoms separated from each other by at least 2 carbon atoms, wherein said heterocycle may optionally contain additional heteroatoms besides nitrogen and/or may be fused to an additional ring system.

Z' may be embodied in a form as defined by Z above, or alternatively may be of the formula

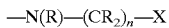

—N(R)—(CR$_2$)$_n$—X wherein
each R is independently H or straight, branched or cyclic alkyl (1–6C),
n is 1 or 2, and
X is an aromatic ring, including heteroaromatic rings, or is a mercaptan;
"linker" represents a bond, alkylene (1–6C) or may comprise aryl, fused aryl, oxygen atoms contained in an alkylene chain, or may contain keto groups or nitrogen or sulfur atoms.

The preferred forms of the compounds of the invention are discussed below.

MODES OF CARRYING OUT THE INVENTION

Figure 1:
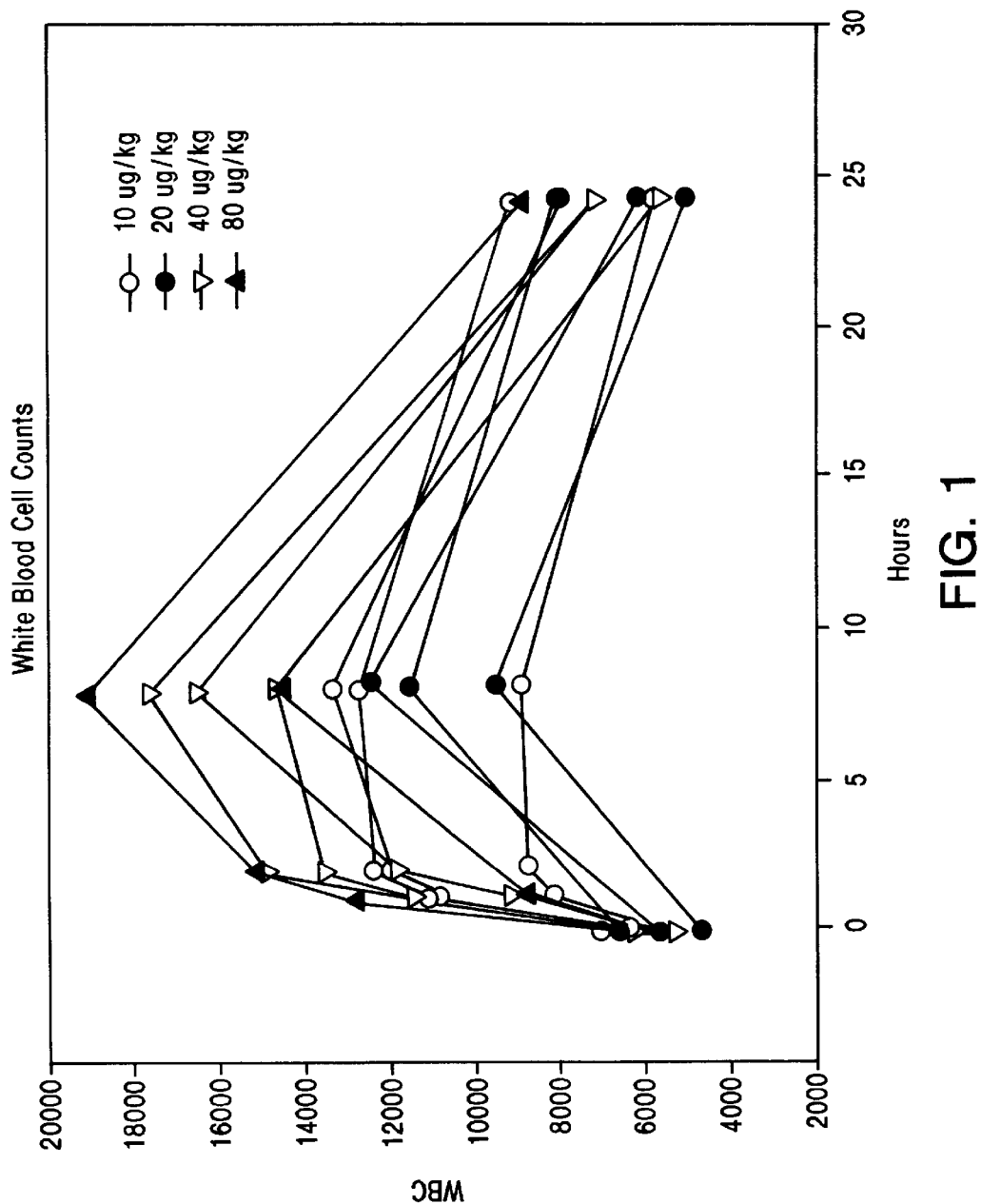
FIG. 1 is a graph showing the response of individual human patients to intravenous administration of a compound of the invention.

The compounds useful in the invention are of the general formula set forth as formula (1) above. Certain embodiments are preferred; included among these are the compounds set forth in the above-incorporated U.S. patents.

In general, preferred embodiments of Z and Z' are cyclic polyamine moieties having from 9–24C that include 3–5 nitrogen atoms. Particularly preferred are 1,5,9,13-tetraazacyclohexadecane; 1,5,8,11,14-pentaazacyclohexadecane; 1,4,8,11-tetraazacylotetradecane; 1,5,9-triazacylcododecane; 1,4,7,10-tetraazacyclododecane; and the like, including such cyclic polyamines which are fused to an additional aromatic or heteroaromatic rings and/or containing a heteroatom other than nitrogen incorporated in the ring. Embodiments wherein the cyclic polyamine contains a fused additional cyclic system or one or more additional heteroatoms are described in U.S. Pat. No. 5,698,546 incorporated hereinabove by reference. Also preferred are 3,7,11,17-tetraazabicyclo(13.3.1)heptadeca-1(17),13,15-triene;
4,7,10,17-tetraazabicyclo(13.3.1)heptadeca-1(17),13,15-triene;
1,4,7,10-tetraazacyclotetradecane; 1,4,7-triazacyclotetradecane; and
4,7,10-triazabicyclo(13.3.1)heptadeca-1(17),13,15-triene.

When Z' is other than a cyclic polyamine as defined in Z, its preferred embodiments are set forth in U.S. Pat. No. 5,817,807, also incorporated hereinabove by reference.

Preferred forms of the linker moiety include those wherein the linker is a bond, or wherein the linker includes an aromatic moiety flanked by alkylene, preferably methylene moieties. Preferred linking groups include the methylene bracketed forms of 1,3-phenylene, 2,6-pyridine, 3,5-pyridine, 2,5-thiophene, 4,4'-(2,2'-bipyrimidine); 2,9-(1,10-phenanthroline) and the like. A particularly preferred linker is 1,4-phenylene-bis-(methylene).

Particularly preferred embodiments of the compound of the formula (1) include 2,2'-bicyclam; 6,6'-bicyclam; the embodiments set forth in U.S. Pat. No. 5,583,131, and in particular 1,1'-[1,4-phenylene-bis(methylene)]-bis-1,4,8,11-tetraazacyclotetradecane, set forth in U.S. Pat. No. 5,021,409, and designated herein AMD3100.

Other preferred embodiments include

N-[1,4,8,11-tetraazacyclotetradecanyl-1,4-phenylenebis(methylene)]-2-aminomethyl)pyridine;
7,7'-[1,4-phenylenebis(methylene)]bis-4,7,10,17-tetraazabicyclo-[13.3.1]heptadeca-1(17),13,15-triene;
7,7'-[1,4-phenylenebis(methylene)]bis-3,7,11,17-tetraazabicyclo[13.3.1]heptadeca-1(17),13,15-triene;
1,1'-[1,3-phenylenebis(methylene)]-bis-1,4,8,11-tetraazacyclotetradecane;
1,1'-[1,4-phenylenebis(methylene)]-bis-1,4,8,11-tetraazacyclotetradecane;
1,1'-[1,4-phenylene-bis-(methylene)]-bis-1,4,7,10-tetraazacyclotetradecane;
1,1'-[1,3-phenylene-bis-(methylene)]-bis-1,4,7,10-tetraazacyclotetradecane;
11,11'-(1,2-propanediyl)bis-1,4,8,11-tetraazacyclotetradecane;
N-[4-(1,4,7-triazacyclotetra-decane)-1,4-phenylenebis(methylene)]-2-(aminomethyl)pyridine;
N-[7-(4,7,10-triazabicyclo[13.3.1]heptadeca-1(17),13,15-triene)-1,4-phenylenebis(methylene)]-2-(aminomethyl)pyridine;
N-[7-(4,7,10,17-tetraazabicyclo[13.3.1]heptadeca-1(17),13,15-triene)-1,4-phenylenebis(methylene)]-2-(aminomethyl)pyridine; and
N-[4-[4,7,10,17-tetraazabicyclo[13.3.1]heptadeca-1(17),13,15-triene]-1,4-phenylenebis(methylene)]-2-(aminomethyl)pyridine.

Methods to synthesize the compounds useful in the method of the invention are set forth in the U.S. patents and application incorporated hereinabove by reference.

The compounds of the invention may be prepared in the form of prodrugs, i.e., protected forms which release the compounds of the invention after administration to the subject. Typically, the protecting groups are hydrolyzed in body fluids such as in the bloodstream thus releasing the active compound or are oxidized or reduced in vivo to release the active compound. A discussion of prodrugs is found in *Smith and Williams Introduction to the Principles of Drug Design,* Smith, H. J.; Wright, $2^{nd}$ ed., London (1988).

The compounds of the invention, as they are polyamines, may be administered prepared in the forms of their acid addition salts or metal complexes thereof. Suitable acid addition salts include salts of inorganic acids that are biocompatible, including HCl, HBr, sulfuric, phosphoric and the like, as well as organic acids such as acetic, propionic, butyric and the like, as well as acids containing more than one carboxyl group, such as oxalic, glutaric, adipic and the like. Typically, at physiological pH, the compounds of the invention will be in the forms of the acid addition salts. Particularly preferred are the hydrobromides. In addition, when prepared as purified forms, the compounds may also be crystallized as the hydrates.

The compounds of the invention may be administered as sole active ingredients, as mixtures of various compounds of formula (1), and/or in admixture with additional active ingredients that are therapeutically or nutritionally useful, such as antibiotics, vitamins, herbal extracts, antiinflammatories, glucose, antipyretics, analgesics, and the like.

The compounds of the invention may be formulated for administration to animal subject using commonly understood formulation techniques well known in the art. Formulations which are suitable for particular modes of administration and for compounds of the type represented by those of formula (1) may be found in *Remington's Pharmaceutical Sciences,* latest addition, Mack Publishing Company, Easton, Pa.

Preferably, the compounds are administered by injection, most preferably by intravenous injection, but also by subcutaneous or intraperitoneal injection, and the like. Additional parenteral routes of administration include intramuscular and intraarticular injection. For intravenous or parenteral administration, the compounds are formulated in suitable liquid form with excipients as required. The compositions may contain liposomes or other suitable carriers. For injection intravenously, the solution is made isotonic using standard preparations such as Hank's solution.

Besides injection, other routes of administration may also be used. The compounds may be formulated into tablets, capsules, syrups, powders, or other suitable forms for administration orally. By using suitable excipients, these compounds may also be administered through the mucosa using suppositories or intranasal sprays. Transdermal administration can also be effected by using suitable penetrants and controlling the rate of release.

The formulation and route of administration chosen will be tailored to the individual subject, the nature of the condition to be treated in the subject, and generally, the judgment of the attending practitioner.

Suitable dosage ranges for the compounds of formula (1) vary according to these considerations, but in general, the compounds are administered in the range of about 0.1

μg/kg–5 mg/kg of body weight; preferably the range is about 1 μg/kg–300 μg/kg of body weight; more preferably about 10 μg/kg–100 μg/kg of body weight. For a typical 70-kg human subject, thus, the dosage range is from about 0.7 μg–350 mg; preferably about 700 μg–21 mg; most preferably about 700 μg–7 mg. Dosages may be higher when the compounds are administered orally or transdermally as compared to, for example, i.v. administration.

The compounds may be administered as a single bolus dose, a dose over time, as in i.v. or transdermal administration, or in multiple dosages.

Subjects that will respond favorably to the method of the invention include medical and veterinary subjects generally, including human patients. Among other subjects for whom the methods of the invention is useful are cats, dogs, large animals, avians such as chickens, and the like. In general, any subject who has a WBC deficiency or, more generally, who would profit from the elevation of white blood cell count is appropriate for administration of the invention method.

Typical conditions which are ameliorated or otherwise benefited by the method of the invention include hematopoietic disorders, such as aplastic anemia, leukemias, drug-induced anemias, and hematopoietic deficits from chemotherapy or radiation therapy. The method of the invention is also useful in enhancing the success of transplantation during and following immunosuppressive treatments as well as in effecting more efficient wound healing and treatment of bacterial inflammation. The method of the present invention is further useful for treating subjects who are immunocompromised or whose immune system is otherwise impaired. Typical conditions which are ameliorated or otherwise benefited by the method of the present invention, include those subjects who are infected with a retrovirus and more specifically who are infected with human immunodeficiency virus (HIV). The method of the invention thus targets a broad spectrum of conditions characterized by a deficiency in white blood cell count, or which would benefit from elevation of said WBC count.

Having now generally described the invention, the same will be more readily understood through reference to the following examples which are provided by way of illustration, and are not intended to be limiting of the present invention, unless specified.

EXAMPLE 1

Clinical Elevation of WBC Levels—Healthy Volunteers

Eleven human patients having initial white blood cell counts of 4,000–6,500 cells/mm$^3$ were used in the study. An intravenous dosing solution of AMD3100 (i.e., 1,1'-[1,4-phenylene-bis(methylene)]-bis-1,4,8,11-tetraazacyclotetradecane) were prepared from a stock solution which is a 1 mg/ml 1:10 dilution of a concentrate in 0.9% saline (normal saline) under sterile conditions. Aliquots from this stock solution were added to 50-ml bags of 0.9% saline for intravenous injection in amounts to achieve the desired dosage levels (10 μg/kg–80 μg/kg).

The subjects described in this example already contained an indwelling peripheral intravenous catheter. The prescribed amount of AMD3100 was administered over 15 minutes by intravenous fusion in a single dose. Blood samples were obtained prior to the dose, and at various times up to 24 hours after dose administration.

Eleven human subjects received intravenous administration of AMD-3100 at doses 10, 20, 40, and 80 μg/kg. Five subjects also received a single subcutaneous injection of AMD-3100 at doses of 40 and 80 μg/kg. The effect of AMD3100 given intravenously in these 11 human subject is shown in FIG. 1. Three patients were administered dosages of 10 μg/kg (open circles); 3 patients were administered dosages of 20 μg/kg (solid circles); 3 patients were administered 40 μg/kg (open triangles); and 2 patients were administered 80 μg/kg (closed triangles).

As shown in FIG. 1, all of the patients at all levels of administration showed a marked increase in white blood cell count over the succeeding 5–10 hours after administration which WBC count tapered off after about 24 hours, although not, in any case, returning to the original level. Generally, the levels of WBC correlate with the concentration levels of the compound in the bloodstream. For example, one patient who received 80 μg/kg experienced an enhancement of white blood cell count from 6,000 cells/mm$^3$ to a peak value of 19,000 cells/mm$^3$. Even the patient showing the least response, who was given 20 μg/kg, experienced an increase from about 6,300 cells/mm$^3$ to about 9,000 cells/mm$^3$.

Thus, it appears that AMD3100 is consistently able to enhance WBC count in human patients.

While not intending to be bound by any theory, the ability to enhance WBC count across various species and the use of various compounds of formula (1) is believed due to the similarity of action of this compound in its antiviral applications and a possible mechanism for enhancing WBC count. The compounds of the invention are believed to exert their antiviral effects by inhibiting the binding of the second receptor for the HIV virus, CXCR-4, and thus to inhibit entry of the virus into the cell. These particular receptors appear homologous throughout a wide range of species, including mouse, rat, cat and man.

EXAMPLE 2

Clinical Elevation of WBC Levels—HIV-Infected Patients

Figure 2:
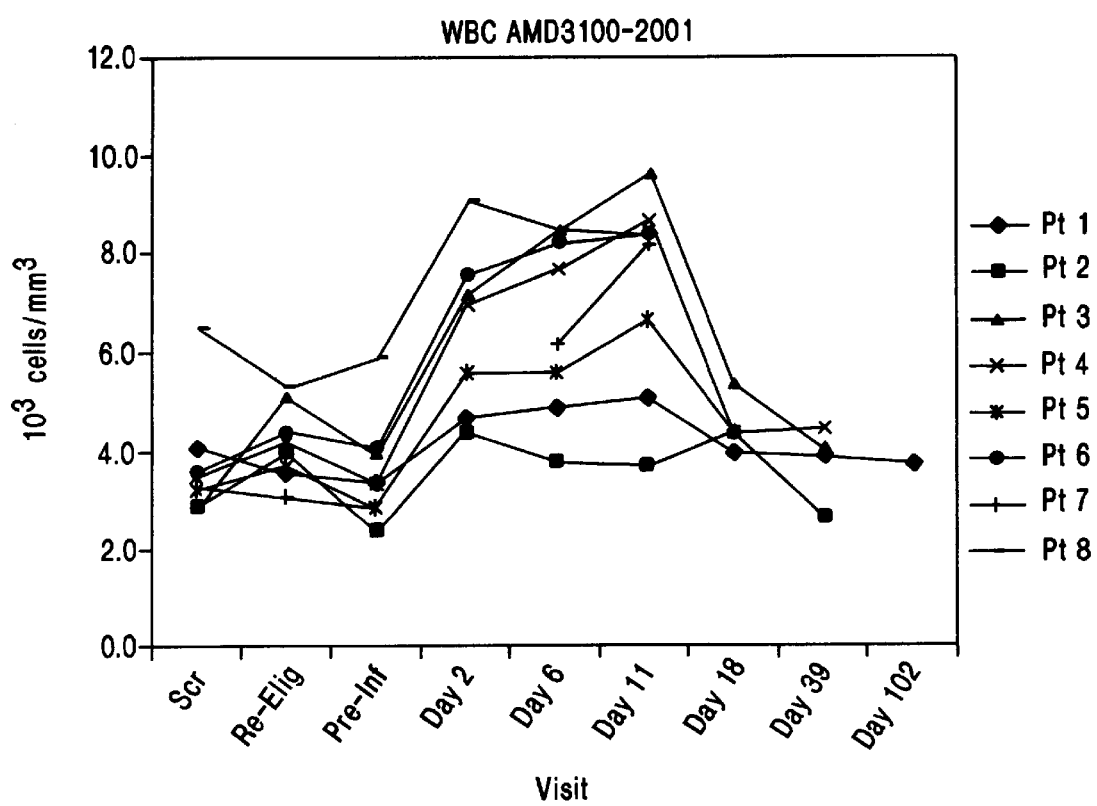
FIG. 2 is a graph showing the response in elevation of WBC counts observed in HIV-infected patients who received AMD-3100 by continuous infusion for up to 10 consecutive days.

Elevations in WBC counts have also been observed in HIV-infected patients who received AMD-3100 by continuous infusion for up to 10 consecutive days (FIG. 2). Eight patients received AMD-3100 at infusion dose rates of 2.5 μg/kg/hr (patients 1–4) and 5.0 μg/kg/hr (patients 5–8). Elevations relative to the baseline were noted in samples taken on days 2, 6, and 11 (immediately prior to end of infusion) of the infusion period. Elevations in WBC count ratios (Day 11 samples) ranged from 1.4 to 2.8 times the baseline. WBC counts returned to baseline 7 days after discontinuation of the infusion. Thus, it appears that AMD3100 is consistently able to enhance WBC count following single dose or with continuous infusion in human patients.

While not intending to be bound by any theory, the ability to enhance WBC count across various species and the use of various compounds of formula (1) is believed due to the similarity of action of this compound in its antiviral applications and a possible mechanism for enhancing WBC count. The compounds of the invention are believed to exert their antiviral effects by inhibiting the binding of the second receptor for the HIV virus, CXCR-4, and thus to inhibit entry of the virus into the cell. These particular receptors appear homologous throughout a wide range of species, including mouse, rat, cat and man.

What is claimed is:

1. A method to treat a subject who would be benefited by elevation of WBC count which method comprises administering to said subject an amount of a compound of the formula Z-linker-Z'  (1)

or pharmaceutically acceptable salt thereof wherein Z is a cyclic polyamine containing 9–32 ring members of which 3–8 are nitrogen atoms, said nitrogen atoms separated from each other by at least 2 carbon atoms, and wherein said heterocycle may optionally contain additional heteroatoms besides nitrogen and/or may be fused to an additional ring system;

Z' may be embodied in a form as defined by Z above, or alternatively may be of the formula —N(R)—(CR$_2$)$_n$—X wherein each R is independently H or straight, branched or cyclic alkyl (1–6C), n is 1 or 2, and X is an aromatic ring, including heteroaromatic rings, or is a mercaptan;

"linker" represents a bond, alkylene (1–6C) or may comprise aryl, fused aryl, oxygen atoms contained in an alkylene chain, or may contain keto groups or nitrogen or sulfur atoms;

in an amount effective to elevate said WBC count in said subject, wherein the subject exhibits a hematopoietic deficit from chemotherapy or radiation therapy, or wherein the subject is a transplantation recipient.

2. The method of claim 1 wherein Z and Z' are both cyclic polyamines.

3. The method of claim 1 wherein Z and Z' are identical.

4. The method of claim 1, wherein Z contains 12–24 members and contains 4 nitrogen atoms.

5. The method of claim 1 wherein Z and Z' are both 1,4,8,11-tetraazocyclotetradecane.

6. The method of claim 1 wherein the linker comprises an aromatic ring bracketed by two methylene moieties.

7. The method of claim 6 wherein the linker is 1,4-phenylene-bis-methylene.

8. The method of claim 7 wherein the compound of formula (1) is 1,1'-[1,4-phenylene-bis-(methylene)-bis-1,4,8,11-tetraazacyclotetradecane (AMD3100).

9. The method of claim 1 wherein the compound of formula (1) is

N-[1,4,8,11-tetraazacyclotetradecanyl-1,4-phenylenebis(methylene)]-2-aminomethyl)pyridine;

7,7'-[1,4-phenylenebis(methylene)]bis-4,7,10,17-tetraazabicyclo-[13.3.1]heptadeca-1(17),13,15-triene;

7,7'-[1,4-phenylenebis(methylene)]bis-3,7,11,17-tetraazabicyclo[13.3.1]heptadeca-1(17),13,15-triene;

1,1'-[1,3-phenylenebis(methylene)]-bis-1,4,8,11-tetraazacyclotetradecane;

1,1'-[1,4-phenylenebis(methylene)]-bis-1,4,8,11-tetraazacyclotetradecane;

1,1'-[1,4-phenylene-bis-(methylene)]-bis-1,4,7,10-tetraazacyclotetradecane;

1,1'-[1,3-phenylene-bis-(methylene)]-bis-1,4,7,10-tetraazacyclotetradecane;

11,11'-(1,2-propanediyl)bis-1,4,8,11-tetraazacyclotetradecane;

N-[4-(1,4,7-triazacyclotetra-decane)-1,4-phenylenebis(methylene)]-2-(aminomethyl)pyridine;

N-[7-(4,7,10-triazabicyclo[13.3.1]heptadeca-1(17),13,15-triene)-1,4-phenylenebis(methylene)]-2-(aminomethyl)pyridine;

N-[7-(4,7,10,17-tetraazabicyclo[13.3.1]heptadeca-1(17),13,15-triene)-1,4-phenylenebis(methylene)]-2-(aminomethyl)pyridine; or N-[4-[4,7,10,17-tetraazabicyclo[13.3.1]heptadeca-1(17),13,15-triene]-1,4-phenylenebis(methylene)]-2-(aminomethyl)pyridine.

10. The method of claim 1 wherein formula (1) is in the form of its acid addition salt.

11. The method of claim 10 wherein the acid addition salt is the hydrobromide.

12. The method of claim 1 wherein the compound is administered to said subject by an intravenous or subcutaneous route.

13. The method of claim 1 wherein the compound of formula (1) is administered to said subject in the dosage range of about 0.1 µg/kg–5 mg/kg of body weight.

14. The method of claim 1, wherein administering the compound of formula (1) to said subject is in a single dose or by continuous infusion.

* * * * *